United States Patent [19]

Holland et al.

[11] 4,112,768

[45] Sep. 12, 1978

[54] DEVICE FOR TAKING A LIQUID SAMPLE

[75] Inventors: Johannes Holland; Hubertus Franciscus Marie Wagemans, both of Eindhoven, Netherlands

[73] Assignee: U.S. Philips Corporation, New York, N.Y.

[21] Appl. No.: 833,153

[22] Filed: Sep. 14, 1977

[30] Foreign Application Priority Data

Sep. 17, 1976 [NL] Netherlands .................. 7610352

[51] Int. Cl.² ........................................... G01N 1/14
[52] U.S. Cl. ................................. 73/422 R; 210/106
[58] Field of Search .................... 73/421 B, 422 R; 210/106, 332, 353, 354

[56] References Cited

U.S. PATENT DOCUMENTS 3,046,791 11/1977 Van Dinteren .................. 73/422 R

FOREIGN PATENT DOCUMENTS 490,486 1/1976 U.S.S.R. ............................ 210/106

*Primary Examiner*—S. Clement Swisher
*Attorney, Agent, or Firm*—Frank R. Trifari; Rolf E. Schneider

[57] ABSTRACT

Analysis of a contaminated liquid by withdrawal of a liquid sample through a filtering element subjected to ultrasonic vibrations generated in the liquid to keep the filtering element clean.

4 Claims, 6 Drawing Figures

DEVICE FOR TAKING A LIQUID SAMPLE

This invention relates to a device for taking a liquid sample from a contaminated liquid stream, comprising a first compartment with an inlet and an outlet for the liquid stream, at least one second compartment with an outlet for the liquid sample, a filter which separates the first and second compartments from each other and means for cleaning the filter.

When analysing a liquid for dissolved or nondissolved constituents a problem which is frequently encountered is that certain constituents contaminate the measuring arrangement. When the liquid moreover contains solid constituents, which are not to be analysed, it is necessary to take steps to prevent precipitation and clogging. Generally, a measuring arrangement is then selected in which the liquid is pumped through the measuring arrangement at a fairly high rate mostly in combination with a centrifugal action. By means of a branch preceded by a filter, a small quantity of liquid can be extracted for analysis purposes. However, the filter then still becomes clogged and soiled after some time. In the case of continuous analysis in unattended measuring stations this effect is completely undesirable. Regular cleaning or replacement of the filter element is then necessary, which renders the maintenance of such stations labour-intensive and expensive.

It is known to automate the cleaning of a filter in such measuring arrangements by periodically passing an amount of the extracted liquid backwards through the filter into the original liquid stream. Owing to this reflux, adhered particles and obstructions are detached from the filter mesh and are drained with the liquid stream. For continuous analysis use is even made of a double arrangement with two filters, of which one filter is cleaned by reflux and the other filter supplies the purified liquid for analysis. By periodic change-over of these functions, a continuous stream of purified liquid can be obtained, each filter being subjected to a cleaning cycle.

A drawback of this arrangement is that a fairly complex pumping arrangement with change-over valves and a control system are necessary.

It is an object of the invention to substantially simplify the cleaning device and for this the invention is characterized in that the means for cleaning the filter incorporates an ultrasonic generator.

In this respect it is advantageous that a continuous cleaning of the filter can be obtained because solid particles can no longer settle on the filter element owing to the presence of the ultrasonic field.

Moreover, the arrangement becomes very compact and contains no moving parts which are subject to wear and which may be sources of leakage.

In one embodiment it is advantageous to incorporate the ultrasonic generator in the wall of the first compartment, preferably opposite the filter, so that the liquid of the liquid stream transmits the vibrations. Arrangements in which the generator is disposed in the second compartment or arrangements in which the filter element via the generator itself vibrates in the liquid are also possible and are assumed to be within the scope of the invention.

It is to be noted that it is known to cause transducers of physical quantities to vibrate in the liquid to be measured in order to clean the measuring surface of the transducer continuously, see U.S. Pat. No. 3,217,543, or to mount several transducers in one compartment and fill this compartment with the liquid to be measured and subsequently periodically energize an ultrasonic generator in the compartment in order to clean all the measuring transducers, see U.S. Pat. No. 3,762,214. It is also known from U.S. Pat. No. 3,056,698 to clean separate fine-mesh filters in a tank with cleaning liquid by means of an ultrasonic generator. However, the present invention relates to cleaning by means of ultrasonic vibrations of a filter which serves as a partition between a stream of contaminated liquid and a sample to be taken from the liquid stream for further processing in analysis equipment.

The invention will be described in more detail with reference to the drawing, in which.

Figure 1:
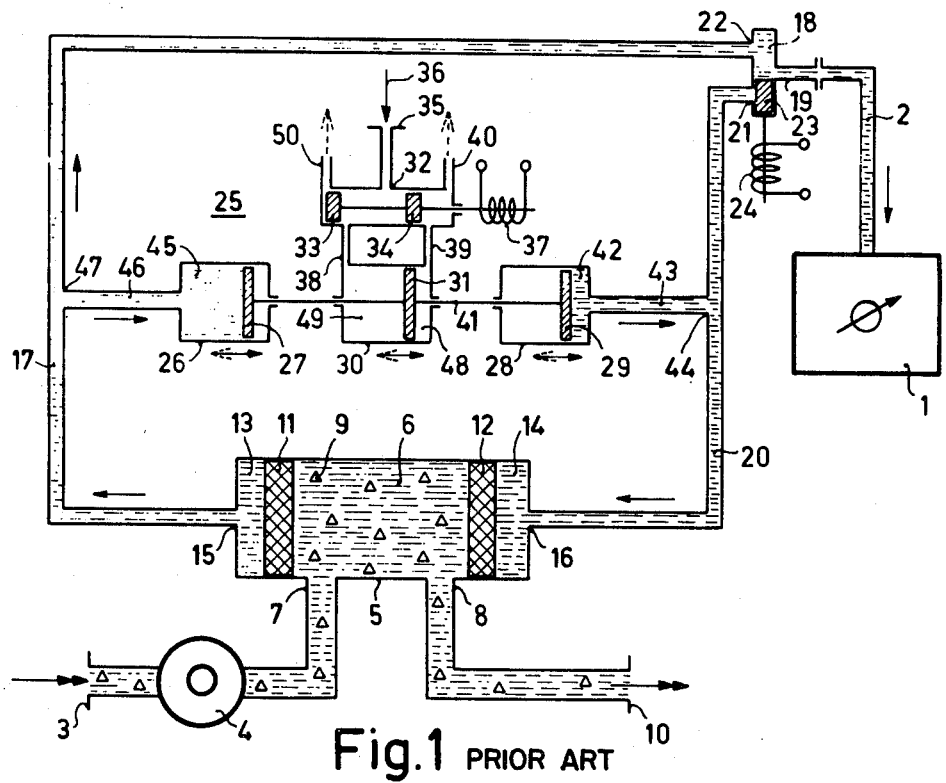
FIG. 1 shows a known measuring arrangement.

The known measuring arrangement of FIG. 1 serves to transfer a liquid which is to be examined for properties, for example of a physical nature, such as conductivity, turbidity, or for chemical composition, into an analysing and measuring apparatus 1 by means of a supply conduit 2. Originally the liquid is highly contaminated and contains particles and constituents which would disturb or prevent analysis. Therefore the liquid must first be purified by means of a filter system. The liquid is supplied at 3 and may be obtained from a storage vessel or from a river or a canal. A pump 4 conveys it to a filter unit 5, which includes a compartment 6 with an inlet connection 7, connected to the pump 4, and an outlet connection 8. A contamination by particles is indicated by 9. The flow rate of the liquid from the inlet 3 through the pump 4, the inlet 7, the compartment 8 and the outlet 10 is selected high, so as to prevent precipitation and settling of the particles 9. A liquid sample is taken alternately through the filter elements 11 and 12 to the compartments 13 and 14 with outlets 15 and 16 respectively. The outlet 15 is connected to a conduit 17 by means of a change-over valve 18, which has an outlet 19 which is connected to the conduit 2. The outlet 16 is connected to the inlet 21 of the change-over valve 18 by a conduit 20. This valve has a switching member 23 which closes the inlet 21 and leaves the inlet 22 open. By means of external actuation, for example an electromagnet 24, the switching member can be moved, so that the inlet 22 is closed and the inlet 21 is open. For cleaning the filter elements 11 and 12 a switching device 25 is provided, which includes a pump cylinder 26 with a plunger 27, a pump cylinder 28 with a plunger 29, an air-pressure cylinder 30 with a plunger 31, and an air-switching valve 32 with coupled plungers 33 and 34. The valve 32 is provided with an inlet connection 35 through which pressurized air is supplied at 36. The plungers 33 and 34 can be moved, for example by energizing an electromagnet 37. In the position shown, the pressurized air flows from the inlet 35 through the valve 32 to a connection 38, which is connected to one side of the cylinder 30, so that the plunger 31 moves to the right. The air at the other side of the cylinder 30 can escape into the atmosphere via a connection 39, the valve 32 and an outlet 40. The plunger 31 is coupled to the plunger 29 of cylinder 28 by a rod 41. As the compartment 42 to the right of the plunger 29 is connected to a branch 44 of the conduit 20 by means of a conduit 43, purified liquid is forced into this conduit. Owing to the position of the switching member 23 in valve 18 this liquid cannot escape therethrough, but it can be forced into compartment 14 of filter unit 5. This purified liquid escapes through filter element 12 into compartment 6 and is thus capable of cleaning the filter from obstructions caused by the particles 9. The plunger 31 is also coupled to the plunger 27 in cylinder 26. This plunger 27 consequently also moves to the right and thus causes the compartment 45 to be filled with purified liquid via conduit 46, which is connected to a branch 47 of conduit 17. This purified liquid is obtained via the filter element 11. After a certain time in which it is assumed that the filter element 12 has been cleaned and filter element 11 is soiled, the magnets 24 and 37 are actuated. The first electromagnet switches the valve 18 from inlet 21 to inlet 22, so that liquid is obtained from conduit 20. The last-mentioned magnet switches over the plungers 33 and 34, so that the pressurized air reaches the compartment 48 via conduit 39 and causes the plunger 31 to move to the left. The air in compartment 49 can now escape via conduit 38 and outlet 50. The liquid in compartment 45 now cleans the filter element 11, and compartment 42 of cylinder 28 is now filled with purified liquid.

Figure 2:
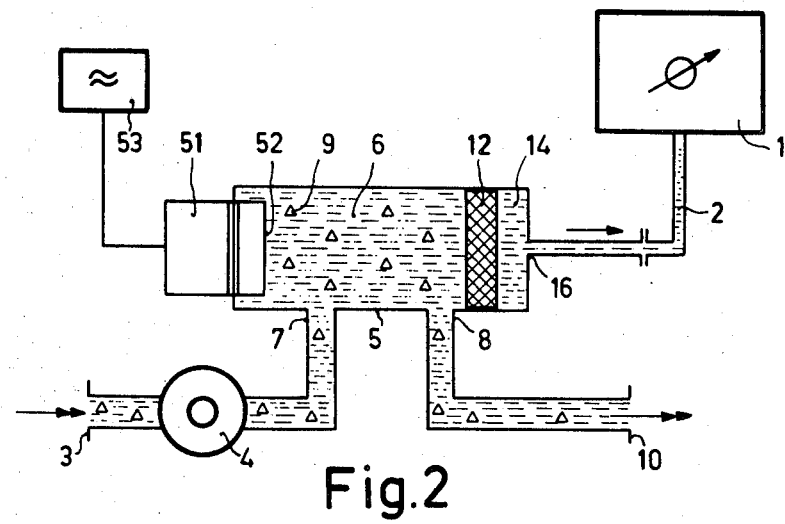
FIG. 2 shows an arrangement in accordance with the invention.

FIG. 2 shows the device in accordance with the present invention. Elements corresponding to those of FIG. 1 bear the same reference numerals. The supply conduit 2 of the analysis device 1 is connected directly to the outlet 16 of filter unit 5. This unit no longer includes the filter element 11. Instead of this a resonator 51 is mounted in the wall, whose active vibrating surface 52 is disposed in the liquid of compartment 6. A generator 53 energizes the resonator 51, so that the surface 52 emits ultrasonic vibrations in the liquid. These vibrations reach the filter element 12, which is thus cleaned in known manner from particles 9 which have settled on it. These particles are discharged by the liquid stream through the outlet 8.

It will be evident that the device in accordance with the invention of FIG. 2 in comparison with that of FIG. 1 results in a substantial reduction in the number of elements, operates far more reliably, hardly demands any maintenance, and is thus less expensive both in respect of purchase and operation.

The analysis device 1 and the ultrasonic section 51, 52 and 53 are known devices, which are described in the cited literature and therefore need not be further described herein.

What is claimed is:

1. Apparatus for taking a liquid sample from a contaminated liquid stream, which comprises a first compartment having an inlet and an outlet for the contaminated liquid stream, a second compartment having an outlet for the liquid sample, a filtering element separating the first compartment and the second compartment from each other, and an ultrasonic generator associated with said compartments for effecting cleaning of the filtering element by means of ultrasonic vibrations generated in the liquid.

2. Apparatus according to claim 3, in which the ultrasonic generator is mounted in a wall of the first compartment.

3. A method of taking a liquid sample from a contaminated liquid stream, which comprises passing the contaminated liquid stream through a first compartment, a second compartment being associated with said first compartment and being separated therefrom by a filtering element, withdrawing the liquid sample through said filtering element from said contaminated liquid stream, and cleaning said filtering element by means of ultrasonic vibrations generated in the liquid.

4. A method according to claim 3, in which the ultrasonic vibrations are generated continuously.

* * * * *

UNITED STATES PATENT OFFICE
CERTIFICATE OF CORRECTION

Patent No. 4,112,768    Dated September 12, 1978

Inventor(s) Johannes Holland et al

It is certified that error appears in the above-identified patent and that said Letters Patent are hereby corrected as shown below:

Col. 4, line 22, After "according to" delete "Claim 3" and insert -- Claim 1 --

Signed and Sealed this

Fourteenth Day of April 1981

[SEAL]

Attest:

RENE D. TEGTMEYER

Attesting Officer        Acting Commissioner of Patents and Trademarks